United States Patent [19]

Haeger et al.

[11] 4,049,809

[45] Sept. 20, 1977

[54] SOLUTION OF A OXAZEPINE FOR ORAL OR PARENTERAL ADMINISTRATION

[75] Inventors: Bruce Edwin Haeger, Highland Mills; James Elwood Krueger; James Alfred Lowery, both of New City; Lawrence Ritter, Suffern, all of N.Y.

[73] Assignee: American Cyanamid Company, Stamford, Conn.

[21] Appl. No.: 734,682

[22] Filed: Nov. 24, 1976

[51] Int. Cl.² .......................................... A61K 31/495
[52] U.S. Cl. .................................................. 424/250
[58] Field of Search ........................................ 424/250

[56] References Cited

U.S. PATENT DOCUMENTS

| 3,412,193 | 11/1968 | Coppola | 424/250 |
|---|---|---|---|
| 3,663,696 | 5/1972 | Havell et al. | 424/250 |

Primary Examiner—Stanley J. Friedman
Attorney, Agent, or Firm—Norton S. Johnson

[57] ABSTRACT

Stable, soluble solutions of 2-chloro-11-(4-methyl-1-piperazinyl)-dibenz[b,f][1,4]oxazepine are described, some of which are suitable for oral and others for parenteral administration.

8 Claims, No Drawings

SOLUTION OF A OXAZEPINE FOR ORAL OR PARENTERAL ADMINISTRATION

CROSS-REFERENCE TO RELATED APPLICATIONS

This application is a substitute application of our earlier application Ser. No. 602,331, filed Aug. 6, 1975, and abandoned Oct. 23, 1976.

BACKGROUND OF THE INVENTION

The compound 2-chloro-11-(4-methyl-1-piperazinyl) dibenz[b,f][1,4]oxazepine is a known compound having therapeutic effects on the central nervous system. U.S. Pat. No. 3,546,226 specifically discloses 2-chloro-11-(4-methyl-1-piperazinyl)-dibenz[b,f][1,4]oxazepine, its nontoxic pharmaceutically acceptable acid addition salts, their parenteral administration and their utility as central nervous system agents. U.S. Pat. 3,663,696 discloses a parenteral solution composed of 2-chloro-11-(1-piperazinyl) dibenz[b,f][1,4]oxazepine and certain acid addition salts thereof, in a mixture of propylene glycol, water and ascorbic acid. U.S. Pat. No. 3,412,193 discloses the oral administration of 2-chloro-11-(4-methyl-1-piperazinyl)-dibenz[b,f][1,4]-oxazepine in propylene glycol for the purpose of testing anti-fertility efficacy.

Problems have existed with preparations containing 2-chloro-11-(4-methyl-1-piperazinyl)-dibenz[b,f][1,4]oxazepine. Due to the compound's low solubility in water, it is difficult to formulate in conventional pharmaceutical forms such as parenteral and oral liquid preparations employing, for example, water for injection. Another problem which makes the compound difficult to prepare in liquid dosage forms in its low solubility in liquids having a basic or near neutral pH. A still further problem associated with the compounds is that one of its hydrolysis products, namely, 2-chloro-dibenz[b,f][1,4]-oxazepin-11(10H)-one, is extremely insoluable in water. Aqueous solutions of 2-chloro-11-(4-methyl-1-piperazinyl)-dibenz[b,f][1,4]oxazepine have proven unstable and unsuitable primarily because of the precipitation of the above hydrolysis product which forms in trace amounts long before the potency of the solution has dropped below acceptable levels. Although the hydrohydrolysis product is nontoxic, its precipitation is, of course, unacceptable in an injectable solution of the active oxazepine. All of the above problems can be overcome by the application of the instant invention.

The oxazepine of this invention and its acid addition salts can be prepared as illustrated in U.S. Pat. No. 3,663,696.

SUMMARY OF THE INVENTION

This invention is concerned with stable oral concentrates and parenteral solutions of 2-chloro-11-(4-methyl-1-piperazinyl)dibenz[b,f][1,4]oxazepine base and its non-toxic pharmaceutically acceptable acid addition salts.

The invention is specifically concerned with an improved solubilized, stabilized solution comprising as the main active ingredient 2-chloro-11-(4-methyl-1-piperazinyl) dibenz[b,f][1,4]oxazepine base or pharmaceutically acceptable acid addition salts thereof dissolved in about 50% to about 80% (preferably about 70% v/v) aqueous solution of propylene glycol having a pH of from about 5.0 to about 7.0 (preferably about 6.0), and, optionally, containing from about 2% to about 10% (preferably about 5%) polysorbate 80. The invention is specifically concerned with parenteral solutions and oral concentrates in accordance with the above.

The invention is further specifically concerned with a method of solubilizing and stabilizing 2-chloro-11-(4-methyl-1-piperazinyl)-dibenz[b,f][1,4]oxazepine which comprises dissolving the compound in about 50% to 80% (preferably 70% v/v) aqueous solutions of propylene glycol, adjusting the pH to about 5.0 to about 7.0 (preferably about 6.0 pH) with a dilute mineral acid such as dilute hydrochloric or sulfuric acid (e.g.. 10%; optionally, adding from about 2% to about 10% (preferably about 5%) polysorbate 80; and adding water to the desired volume (water for injection in the case of parenterals). Such as procedure has the advantages of providing a stable, pharmaceutically acceptable solution of the active oxazepine, wherein: solution is complete and remains so for prolonged periods; the pH is conductive to maintaining solution and is not incompatible for either oral or parenteral administration; the stability is good; and traces of the noted hydrolysis product remain in solution.

In addition of Polysorbate 80 at a level of about 2% to about 10%, although not absolutely necessary, provides an additional advantage for both the parenteral solution and oral concentrate. Because 2-chloro-11-(4-methyl-1-piperazinyl)-dibenz[b,f][1,4]oxazepine crystallizes from neutral or basic media, the oxazepine exhibits a tendency to crystallize when parenterally administered to body fluids (pH about 7.0). The addition of Polysorbate 80 raises the solubility level of the oxazepine in the 70% aqueous propylene glycol and eliminates the crystallization during intramuscular administration. The addition of Polysorbate 80 to the oral concentrate is advantageous when it is desired to add the concentrate to non-acidic foods or beverages because the oxazepine precipitates on dilution with such foods unless polysorbate 80 is present.

The compound 2-chloro-11-(4-methyl-1-piperazinyl)-dibenz[b,f][1,4]oxazepine may be employed in the solutions of this invention either in the form of its free base or its non-toxic, pharmaceutically acceptable acid addition salts, preferably the succinate salt. Other non-toxic pharmaceutically acceptable acid accition salts deemed suitable in addition to the succinate included the hydrochloride, sulfate, phosphate, citrate, tartrate, maleate, fumerate, heptanoate, pamoate, etc.

DETAILED DESCRIPTION OF THE INVENTION

A parenteral solution of the invention may be prepared as follows. The concentrations of ingredients are based on the final volume unless otherwise defined. 2-Chloro-11-(4-methyl-1-piperazinyl)-dibenz[b,f][1,4-]oxazepine in an amount sufficient to provide a final weight percent/volume of 0.5% to 5% (5 mg/cc to 50 mg/cc) is dissolved in 50% to 80% v/v of propylene glycol U.S.P. The solution is adjusted to pH 5.0 to 7.0 with a dilute mineral acid, diluted to 100% with water for injection U.S.P. and then sterile filtered. If desired, Polysorbate 80 U.S.P. at 2% to 10% may be added to the propylene glycol solution before diluting to final volume with water for injection.

A oral concentrate of the invention may be prepared in the same manner as above except that sterilization is not needed and distilled water may be substituted for water for injection.

The oral concentrate can be added to foods for the purpose of producing a palatable form of the oxazepine or for concealing its presence, e.g., for administration to patients who may reject the drug if aware of it. Such patients include mentally disturbed persons, as in mental hospitals; children; senile persons; etc. Although a variety of foods can be used for these purposes, liquid foods are especially adaptable and particularly fruit juices, such as orange juice and related beverages. Oral concentrates containing about 10-50 mg of drug per ml of concentrate may be used with about 25 mg/ml being preferred. The oral concentrate may be added to foods in amounts of up to 2 ml of concentrate per ounce of food with about 0.5-1.0 ml/ounce being preferred. The total amount of concentrate will of course depend on the nature of the illness and on the patient, but, in general, from one half to 6 ml of concentrate, containing for example 25 mg/ml, may be used per day, with a preferred range of 2 to 4 ml. Such amount may be given in one dose or divided into 2, 3 or 4 doses which are given at appropriate intervals.

EXAMPLE 1

Preparation of Parenteral Solution of 2-Chloro-11-(4-methyl-1-piperazinyl)-dibenz[b,f][1,4]-oxazepine Base A 63.0 gm portion of 2-chloro-11-(4-methyl-1-piperazinyl)-dibenz[b,f]1,4]oxazepine base is added to 2100 ml of propylene glycol U.S.P. grade and mixed. An 800 ml portion of water for injection is added and mixed. The pH is adjusted to 6.2 with 10% hydrochloric acid, mixed and heated to 60°C. for 30 minutes. The pH is adjusted to 6.0 with 10% hydrochloric acid (making the total volume of hydrochloric acid used 51 ml). The mixture is diluted to 3000 ml with water for injection and sterile filtered through a 293 mm Selas filter or its equivalent having a 0.22$\mu$ membrane. The final solution has a potency of 2.0% active ingredient.

The formulation is filled into ampoules or vials each containing 2.0 ml (representing 40 mg of drug).

EXAMPLE 2

Preparation of Parenteral Solution of 2-Chloro-11-4-methyl-1-piperazinyl)-dibenz[b,f][1,4]oxazepine Base A 105.63 gm portion of 2-chloro-11-(4-methyl-1-piperazinyl)-debenz[b,f][1,4]oxazepine base is added to a mixture of 1400 ml of propylene glycol U.S.P. and 400 ml of water for injection and mixed. The pH is adjusted to 6.0 with 10% hydrochloric acid. A 100 gm portion of Polysorbate 80 U.S.P. is added. The pH is readjusted to 6.0 with 10% hydrochloric acid and the solution is diluted to 2000 ml with water for injection. The solution is filtered through a Millipore AP20 pad and then Selas 0.2$\mu$ silver membrane or its equivalent. The final solution has a potency of 5.0% active ingredient.

The formulation is filled into ampoules or vials each containing 2.0m (representing 100 mg of drug).

EXAMPLE 3

Preparation of an Oral Concentrate of 2-Chloro-11-(4-methyl-1-piperazinyl)-dibenz[b,f][1,4]-oxazepine Base A 12,600 ml portion of propylene glycol U.S.P. is placed in a 25 liter stainless steel pot. A 4 liter portion of water is added and mixed. A 474 gm portion of 2-chloro-11-(4-methyl-1-piperazinyl)-dibenz[b,f][1,4]oxazepine base is added and mixed. The pH of the solution is adjusted to 6.0 with 10% hydrochloric acid. This solution is diluted to 18,000 ml with water; mixed, the pH is readjusted to 6.0 and then filtered through a Millipore AP 20 pad and 0.45 to 1.2 micron solvent resistant membrane. The potency of the final solution is 2.5% as active ingredient.

EXAMPLE 4

Use of Oral Concentrate of 2-Chloro-11-(4-methyl-1-piperazinyl)-dibenz[b,f][1,4]-oxazepine Base An oral concentrate containing 2.5% w/v 2-chloro-11-(4-methyl-1-piperazinyl)-dibenz[b,f][1,4]oxazepine base in 70% aqueous propylene glycol, prepared as in Example 3, was added to grapefruit, orange, or pineapple juice, adding 1 ml of concentrate per ounce of juice (0.83 mg of drug per ml of drink). The taste, appearance, and pH of the drinks were acceptable and the stability was satisfactory for at least 24 hours in the juices named.

EXAMPLE 5

Typical formulations are:

| Parenteral | Percent w/v |
|---|---|
| 2-chloro-11-(4-methyl-1-piperazinyl)-dibenz[b,f][1,4]oxazepine base | 5.25 |
| Polysorbate 80 USP Food Additive Grade | 5.0 |
| Hydrochloric Acid - Reagent q.s. pH 6.0 | q.s. |
| Propylene Glycol USP | 70.0 (v) |
| Water for injection USP q.s. ad | 100.0 (v) |
| Oral | |
| 2-chloro-11-(4-methyl-1-piperazinyl)-dibenz[b,f][1,4]oxazepine base | 2.63 |
| Hydrochloric Acid - Reagent q.s. pH 6.0 | q.s. |
| Propylene Glycol USP | 70.0 (v) |
| Water (Distilled) | 100.0 (v) |

Other ingredients which do not adversely affect the parenteral solution or oral concentrate may also be added thereto such as buffers, preservatives, flavors, dyes, sweetening agents, suspending agents, and the like. Also, minor amounts of other active ingredients may be added as long as they do not adversely affect the solution or concentrate.

The efficacy of the solutions of 2-chloro-11-(4-methyl-1-piperazinyl)-dibenz[b,f][1,4]oxazepine, prepared in accordance with the present invention, may be illustrated by a comparison of their potency with the encapsulated form of this compound. For such a test, male Wistar strain rats are used. Capsule contents comprising 2-chloro-11-(4-methyl-1-piperazinyl)-dibenz[b,f][1,4]oxazepine succinate and conventional excipients is suspended in a 2% starch vehicle and administered to rats by gavage at the rate of 0.5 ml per 100 gm of body weight. Nine dose levels ranging from 0.06 to 12.0 mg/kg are used with 10 to 15 rats per dose. A parenteral solution comprising 2-chloro-11-(4-methyl-1-piperazinyl)-dibenz-[b,f][1,4]oxazepine base at a concentration of 20 mg/ml in 70% propylene glycol is injected into rats undiluted, intramuscularly in micro liter volumes. Eight dose levels ranging from 0.12 to 12.0 mg/kg are used with 10 to 40 rats per dose.

Each rat is tested for catalepsy, a measure of the neuroleptic activity of the drug, at various times up to 6 hours after drug administration. The criterion for catalepsy is maintenance of paw position on four corks for longer than 10 seconds. The median effective doses, those at which 50% of the animals showed catalepsy, is calculated at various intervals of time after drug administration.

The results appear in Table I.

TABLE I

| Hours After Administration | Median Effective Dose (ED$_{50}$) (95% Confidence Limits) | |
|---|---|---|
| | Capsule Suspension (Succinate) | Parenteral Solution Base |
| 0.25 | 12.0 (6.7–21.6) | 7.0 (4.7–10.3) |
| 0.5 | 2.1 (1.4–3.4) | 2.8 (2.1–3.8) |
| 0.75 | 0.57(0.36–0.91) | 0.97(0.65–1.5) |
| 1.0 | 0.32(0.20–0.52) | 0.50(0.40–0.62) |
| 1.5 | 0.21(0.14–0.31) | 0.36(0.27–0.48) |
| 3.0 | 0.15(0.09–0.24) | 0.19(0.15–0.24) |
| 6.0 | 0.12(0.07–0.20) | 0.15(0.11–0.21) |

The above results show that there are no real differences in potency between the oral (capsule) and parenteral (intramucular) forms at any time period up to 6 hours after drug administration.

The favoarable stability of the oral and parenteral solutions of this invention have been established in numerous tests. The criterion of stability being the lack of precipitation of the hydrolysis product 2-chloro-dibenz[b,f][1,4]oxazepin-11(1OH)-one. In general, crystallization of this hydrolysis product does not occur at concentrations below 500 mcg/ml in these new solutions. Three such studies follow:

In the first study a number of 10 mg/ml solutions of 2-chloro-11-(4-methyl-1-piperazinyl)-dibenz[b,f][1,4]oxazepine base are prepared in 50%, 60% and 70% aqueous propylene glycol at pH 6.0. A 15 month stability study produced the composite results shown in Table II.

TABLE II

| Propylene Glycol Content | Hydrolysis Product (mcg/ml) | Potency of Active Component As % of Initial Potency |
|---|---|---|
| 50% | 120 | 98.2 |
| 60% | 110 | 98.3 |
| 70% | 100 | 98.5 |

All of the solutions retain acceptable potency levels and none show precipitation of the hydrolysis product.

In the second study a parenteral solution of 2-chloro-11-(4-methyl-1-piperazinyl)-dibenz[b,f][1,4]oxazepine is prepared at a concentration of 15 mg/ml in 70% v/v propylene glycol in water for injection U.S.P. at a pH of 6.0. A stability study is carried out at various temperatures and for varying lengths of time, as indicated in Table III, to measure the retained potency of the active component as well as the increase in concentration of the hydrolysis product.

TABLE III

| Storage Condition | | Potency (mg/ml) | Hydrolysis Product (mcg/ml) | Physical Appearance |
|---|---|---|---|---|
| Fresh | | 16.0 | 26 | Clear |
| Room Temp. | 2 Months | 15.4 | 55 | " |
| | 4 | 15.6 | 67 | " |
| | 6 | 15.6 | 94 | " |
| | 11 | 15.4 | 142 | " |
| | 13 | 15.1 | 144 | " |
| | 18 | 14.3 | 260 | " |
| 42° C | 1 Month | 16.0 | 124 | " |
| | 2 | 14.5 | 192 | " |
| | 4 | 15.5 | 340 | " |
| 56° C | 2 Weeks | 15.3 | 163 | " |
| | 1 Month | 16.0 | 320 | " |
| | 2 | 14.5 | 580 | " |
| 70° C | 1 Week | 15.0 | 370 | Precipitate |
| | 2 | 14.8 | 467 | " |

In the third test a parenteral solution of the active ingredient at a concentration of 20 mg/ml was prepared as described in the second stability study. The results appear in Table IV.

TABLE IV

| Storage Condition | | Potency (mg/ml) | Hydrolysis Product (mcg/ml) | Physical Appearance |
|---|---|---|---|---|
| Fresh | | 21.6 | 33.0 | Clear |
| Room Temp. | 2 Months | 21.1 | 62.7 | " |
| | 4 | 22.3 | 78 | " |
| | 6 | 20.8 | 116 | " |
| | 11 | 20.7 | 160 | " |
| | 13 | 20.6 | 184 | " |
| | 18 | 20.5 | 340 | " |
| 42° C | 1 Month | 21.8 | 146 | " |
| | 2 | 20.5 | 232 | " |
| | 4 | 20.2 | 436 | " |
| 56° C | 2 Weeks | 21.0 | 185 | " |
| | 1 Month | 20.6 | 374 | " |
| | 2 | 19.4 | 732 | " |
| 70° C | 1 Week | 20.7 | 480 | Precipitate |
| | 2 | 20.6 | 623 | " |

As can be seen from the second and third stability studies, the solutions of this invention show excellent stability even under accelerated conditions.

We claim:

1. A solubilized and stabilized solution comprising 2-chloro-11-(4-methyl-1-piperazinyl)-dibenz[b,f][1,4]oxazepine, or a pharmaceutically acceptable acid-addition salt thereof, in about 50% to about 80% v/v aqueous solution of propylene glycol having a pH of from about 5.0 to about 7.0.

2. A solution in accordance with claim 1, additionally containing from about 2% to about 10% polysorbate 80.

3. A solution in accordance with claim 1, for use as a oral concentrate.

4. A solution in accordance with claim 1, for use as a parenteral solution.

5. A solution in accordance with claim 2, for use as a parenteral solution.

6. A solution in accordance with claim 2, for use as a oral concentrate.

7. A method of preparing a solubilized and stabilized solution containing 2-chloro-11-(4-methyl-1-piperazinyl)-dibenz[b,f][1,4]oxazepine, or a pharmaceutically acceptable salt thereof, which comprises dissolving said oxazepine or salt thereof in about 50% to about 80% v/v aqueous solution of propylene glycol; adjusting the pH to about 5.0 to about 7.0 with a dilute mineral acid; and adding water to the desired volume.

8. A method according to claim 7, which involves the additional step of adding from about 2% to about 10% polysorbate 80.

* * * * *